(12) United States Patent
Trout et al.

(10) Patent No.: US 7,322,992 B2
(45) Date of Patent: Jan. 29, 2008

(54) METHOD OF REMOVING A FASTENER

(75) Inventors: Hugh Trout, Washington, DC (US); Howard M. Tanner, Logan, UT (US)

(73) Assignee: EVA Corporation, Bethesda, MD (US)

( * ) Notice: Subject to any disclaimer, the term of this patent is extended or adjusted under 35 U.S.C. 154(b) by 0 days.

(21) Appl. No.: 10/173,660

(22) Filed: Jun. 19, 2002

(65) Prior Publication Data
US 2002/0198536 A1    Dec. 26, 2002

Related U.S. Application Data

(60) Provisional application No. 60/299,188, filed on Jun. 20, 2001.

(51) Int. Cl.
*A61B 17/10* (2006.01)

(52) U.S. Cl. ............ 606/138; 606/139; 606/155; 623/1.36

(58) Field of Classification Search ........ 606/113, 606/138, 151, 155, 139, 205, 206, 207, 208, 606/209, 170, 232, 200; 623/1, 12, 194, 623/195, 213, 1.36; 200/138, 139, 140; 227/19, 227/175, 181
See application file for complete search history.

(56) References Cited

U.S. PATENT DOCUMENTS

| | | | | |
|---|---|---|---|---|
| 591,403 A * | 10/1897 | Hoffmann | ............... | 606/137 |
| 4,098,157 A | 7/1978 | Doyle | | |
| 4,326,530 A * | 4/1982 | Fleury, Jr. | ............. | 128/303.14 |
| 4,512,338 A * | 4/1985 | Balko et al. | ............. | 128/1 R |
| 4,562,596 A * | 1/1986 | Kornberg | ................. | 623/1 |
| 4,787,899 A * | 11/1988 | Lazarus | .................. | 623/1 |
| 5,042,707 A * | 8/1991 | Taheri | .................. | 606/213 |
| 5,312,420 A * | 5/1994 | Toso et al. | ............ | 606/138 |
| 5,334,196 A * | 8/1994 | Scott et al. | ............ | 606/138 |
| 5,403,326 A * | 4/1995 | Harrison et al. | ............ | 606/139 |
| 5,462,561 A * | 10/1995 | Voda | ................ | 606/144 |
| 5,565,122 A | 10/1996 | Zinnbauer et al. | | |
| 5,707,377 A | 1/1998 | Keller et al. | | |
| 5,749,918 A * | 5/1998 | Hogendijk et al. | ............ | 623/1 |
| 5,788,716 A * | 8/1998 | Kobren et al. | ............ | 606/141 |
| 5,843,160 A * | 12/1998 | Rhodes | .................. | 623/1 |
| 5,957,940 A * | 9/1999 | Tanner et al. | ............ | 606/155 |
| 5,984,939 A * | 11/1999 | Yoon | ................. | 606/170 |
| 6,004,330 A | 12/1999 | Middleman et al. | | |
| 6,106,532 A * | 8/2000 | Koike et al. | ............ | 606/138 |
| 6,375,661 B2 * | 4/2002 | Chu et al. | .............. | 606/113 |

* cited by examiner

*Primary Examiner*—Anhtuan T. Nguyen
*Assistant Examiner*—Ryan Severson
(74) *Attorney, Agent, or Firm*—John N. Coulby; Kelley Drye & Warren LLP

(57) ABSTRACT

The present invention relates generally to a surgical instrument. In particular, the present invention relates to a fastener remover for use during the repair of abdominal aortic aneurysms. The fastener remover, in accordance with an embodiment of the present invention, comprises an outer catheter, an inner sheath, and a gripping member. The outer catheter comprises a hollow passage with a proximal end and a distal end. The inner sheath is disposed within the hollow passage of the outer catheter, extending from the outer catheter's proximal end to the distal end. The gripping member is located within the inner sheath, extending from the outer catheter's proximal end to the distal end. The gripping member comprises a connector portion connected to an elongated stem.

4 Claims, 2 Drawing Sheets

METHOD OF REMOVING A FASTENER

CROSS-REFERENCE TO RELATED APPLICATIONS

The present invention relates to, and is entitled to the benefit of the earlier filing date and priority of, U.S. Provisional Application Ser. No. 60/299,188, filed Jun. 20, 2001.

FIELD OF INVENTION

The present invention relates generally to a surgical instrument. In particular, the present invention relates to a fastener remover for use during a surgical procedure, such as, but not limited to, the repair of abdominal aortic aneurysms.

BACKGROUND OF THE INVENTION

An aneurysm is a ballooning of the wall of an artery resulting from the weakening of the artery due to disease or other conditions. Left untreated, the aneurysm will frequently rupture, resulting in loss of blood through the rupture and death.

Aortic aneurysms are the most frequent form of arterial aneurysm and are life threatening. The aorta is the main artery, which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of aortic aneurysm larger than about 5 cm in diameter in this section of the aorta is ominous. Left untreated, the aneurysm may rupture, resulting in rapid, and usually fatal, hemorrhaging. Typically, a surgical procedure is not performed on aneurysms smaller than 5 cm because presently no statistical benefit exists in performing such procedures.

Aneurysms in the abdominal aorta are associated with a particularly high mortality rate; accordingly, current medical standards call for urgent operative repair. Abdominal surgery, however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the aortic aneurysm. A prosthetic device, typically a synthetic tube graft, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, apparatus and method development have attempted to treat an aortic aneurysm without the attendant risks of intra-abdominal surgical intervention. Among them are inventions disclosed and claimed in Kornberg, U.S. Pat. No. 4,562,596 for Aortic Graft, Device and Method for Performing an Intraluminal Abdominal Aortic Aneurysm Repair; Lazarus, U.S. Pat. No. 4,787,899 for Intraluminal Graft Device, System and Method; and Taheri, U.S. Pat. No. 5,042,707 for Intravascular Stapler, and Method of Operating Same.

Kornberg discloses an aortic graft comprising a flexible tubular material having a plurality of struts to lend the graft stability and resiliency. The struts have angled hooks with barbs at their upper ends which are securely attached to the inside of the aorta above the aneurysm. Kornberg's graft is inserted using a tubular device also disclosed in his patent. Kornberg, however, only anchors the proximal end of the graft. Kornberg claims that the downward flow of blood holds the distal graft securely in place, so that no mechanical attachment is necessary distally. The blood pressure in the abdominal aorta, however, is typically in the magnitude of 130 mm of mercury (Hg). In spite of the direction of flow of blood through the graft, proximal to distal, substantial back pressure within the aneurysm will result unless the distal end is also mechanically attached to the aorta in a manner that prevents substantial leakage of blood between the graft and the aorta. Without distal attachment, the device of Kornberg will not effectively exclude the weakened arterial wall at the site of the aneurysm from the forces and stress associated with the blood pressure.

Lazarus discloses a grafting system that employs a plurality of staples mounted in the proximal end of the graft. Lazarus's staples are forced through the aorta wall by means of a balloon catheter. As does Kornberg, Lazarus discloses staples mounted only in the proximal end of the graft. There is no teaching or suggestion in Lazarus, U.S. Pat. No. 4,787,899 as to the desirability of, let alone means for, mechanically attaching the graft to the distal aorta below the level of the aneurysm.

Taheri discloses an articulatable stapler for implanting a graft in a blood vessel. The stapler is in the form of an elongated catheter with a plurality of segments mounted on the distal end of the catheter. The segments have beveled faces and are connected to each other by hinges. A stylet runs through the catheter to the most distal segment. The most distal segment is moved, in conjunction with the other segments, into a firing position that is substantially perpendicular to the main catheter body by the action of pulling on the stylet. The staple is implanted by using two other stylets, which act as fingers to bend the staple into its attachment position.

Taheri, however, appears to be a single-fire design which can only implant one staple at a time. After each stapler is implanted, Taheri's design apparently requires that the catheter be removed before another staple is loaded. In addition, Taheri's does not teach or suggest an appropriate density of staples to secure a graft against the pulsatile blood flow of the aorta. Pressures within the aorta range from 120 mm Hg pressure to 200 mm Hg pressure. Without adequate attachment, the graft may leak around the edges continuing to allow life threatening pressures to develop in the aneurysm, and may not even remain in place.

During a surgical procedure a suture normally may be used to attach a surgical component to a vessel. Alternatively, an innovative fastener disclosed in U.S. Pat. Nos. 5,957,940 and 5,997,556 reveal a fastener assembly having a flexible fastening means under a compressive force. The fastener comprises a spring assembly of coils having a first portion adapted to be positioned on one side of the surgical component and the vessel wall, a second portion adapted to be positioned on another side of the surgical component and the vessel wall, and an intermediate portion connecting the first portion and the second portion, the intermediate portion extending through the vessel wall and the surgical component. Although the innovative fastener is directed to a new and improved method of repairing an abdominal aortic aneurysm, a problem persists as to removing this particular fastener when misplacement occurs. Additionally, it would be beneficial to decrease any damage to the surrounding vessel wall and surgical component without discomforting the surgical patient.

What is needed, therefore, is an extractor that accommodates the recently inserted innovative fasteners that may have been misplaced or otherwise require removal. Specifically, the extractor should be used to manipulate the innovative fastener so that the surgical procedure can continue as planned rather than having to discontinue the procedure and convert the procedure into an open operation for removal of the fasteners.

It is therefore an advantage of some, but not necessarily all, embodiments of the present invention to provide a fastener remover for removing an inserted surgical fastener during a surgical procedure.

It is another advantage of embodiments of the present invention to provide a fastener remover for removing a surgical fastener when misplacement occurs.

It is another advantage of embodiments of the present invention to provide a fastener remover that decreases damage to the surrounding vessel wall and surgical component during removal.

It is yet another advantage of embodiments of the present invention to provide a fastener remover that allows for fastener removal during a surgical procedure without the need for converting the procedure into an open operation.

Additional advantages of various embodiments of the invention are set forth, in part, in the description that follows and, in part, will be apparent to one of ordinary skill in the art from the description and/or from the practice of the invention.

SUMMARY OF THE INVENTION

Responsive to the foregoing challenges, Applicant has developed an innovative fastener remover for use during a surgical procedure. According to an embodiment of the present invention, the fastener remover comprises: at least one catheter sheath having a hollow passage therein; and a gripping member located within the hollow passage of the at least one catheter sheath, wherein the gripping member comprises a connector portion connected to an elongated stem.

The connector portion may engage the fastener such that the fastener is extracted. The fastener remover may further comprise a cutting member located within the hollow passage of the at least one catheter sheath, wherein the cutting member engages the fastener such that the fastener is severed. The connector portion may comprise a hook, a plurality of longitudinally extending flanges, a spike, a retractable ring, or forceps.

According to another embodiment of the present invention, the fastener remover for manipulating at least one fastener comprises: an outer catheter having a hollow passage therein with a proximal end and a distal end; an inner sheath disposed within the hollow passage of the outer catheter extending from the proximal end to the distal end of the outer catheter; and a gripping member located within the inner sheath extending from the proximal end to the distal end of the outer catheter, wherein the gripping member comprises a connector portion connected to an elongated stem.

According to this embodiment, the connector portion may engage the fastener such that the fastener is extracted. The fastener remover may further comprise a cutting member located within the inner sheath, wherein the cutting member engages the fastener such that the fastener is severed. The connector portion may comprise a hook, a plurality of longitudinally extending flanges, a spike, a retractable ring, or forceps.

In another embodiment of the present invention, a fastener remover for manipulating at least one fastener integral with a surgical component and a vessel wall comprises: an outer catheter having a hollow passage therein with a proximal end and a distal end, the outer catheter extending to a site of extraction; an inner sheath disposed within the hollow passage of the outer catheter, the inner sheath extending from the proximal end to the distal end of the outer catheter; and a gripping member located within the inner sheath extending from the proximal end to the distal end of the outer catheter, the gripping member comprising a connector portion connected to an elongated stem, wherein the connector portion procures the fastener from the surgical component and the vessel wall.

According to this embodiment of the present invention, the connector portion may engage the fastener such that the fastener is extracted. The fastener remover may further comprise a cutting member located within the inner sheath, wherein the cutting member engages the fastener such that the fastener is severed.

The present invention is also directed to a method of extracting an inserted fastener at a surgical site with a fastener remover, comprising the steps of: aligning the fastener remover with the fastener to be removed; and engaging the fastener remover to procure the fastener.

The step of engaging the fastener remover may further comprise the steps of: gripping the fastener with a connector portion of the fastener remover; and adding a force with the fastener remover to disengage the fastener such that the fastener is removed from the surgical site. The step of adding a force with the fastener remover to disengage the fastener may further comprise the step of pulling the fastener through a surgical component and a vessel wall between which the fastener was interposed.

The step of engaging the fastener remover may further comprise the step of severing the fastener with a cutting member of the fastener remover. The step of severing the fastener may further comprise the step of severing the fastener flush with a surgical component, wherein the inserted fastener was interposed between the surgical component and a vessel wall.

It is to be understood that both the foregoing general description and the following detailed description are explanatory only, and are not restrictive of the invention, as claimed. The accompanying drawings, which are incorporated herein by reference, and which constitute a part of this specification, illustrate certain embodiments of the invention and, together with the detailed description, serve to explain the principles of those embodiments of the present invention.

BRIEF DESCRIPTION OF THE DRAWINGS

In order to assist the understanding of this invention, reference will now be made to the appended drawings, in which like reference characters refer to like elements. The drawings are exemplary only, and should not be construed as limiting the invention.

DETAILED DESCRIPTION OF EMBODIMENTS OF THE INVENTION

The present invention will now be described in connection with the surgical repair of an aneurysm. The invention, however, is not limited solely to use in the repair of an aneurysm with a surgical component, such as, but not limited to, a prosthetic graft; rather, it is contemplated that a fastener remover according to the present invention may be used in other surgical procedures.

Figure 1:
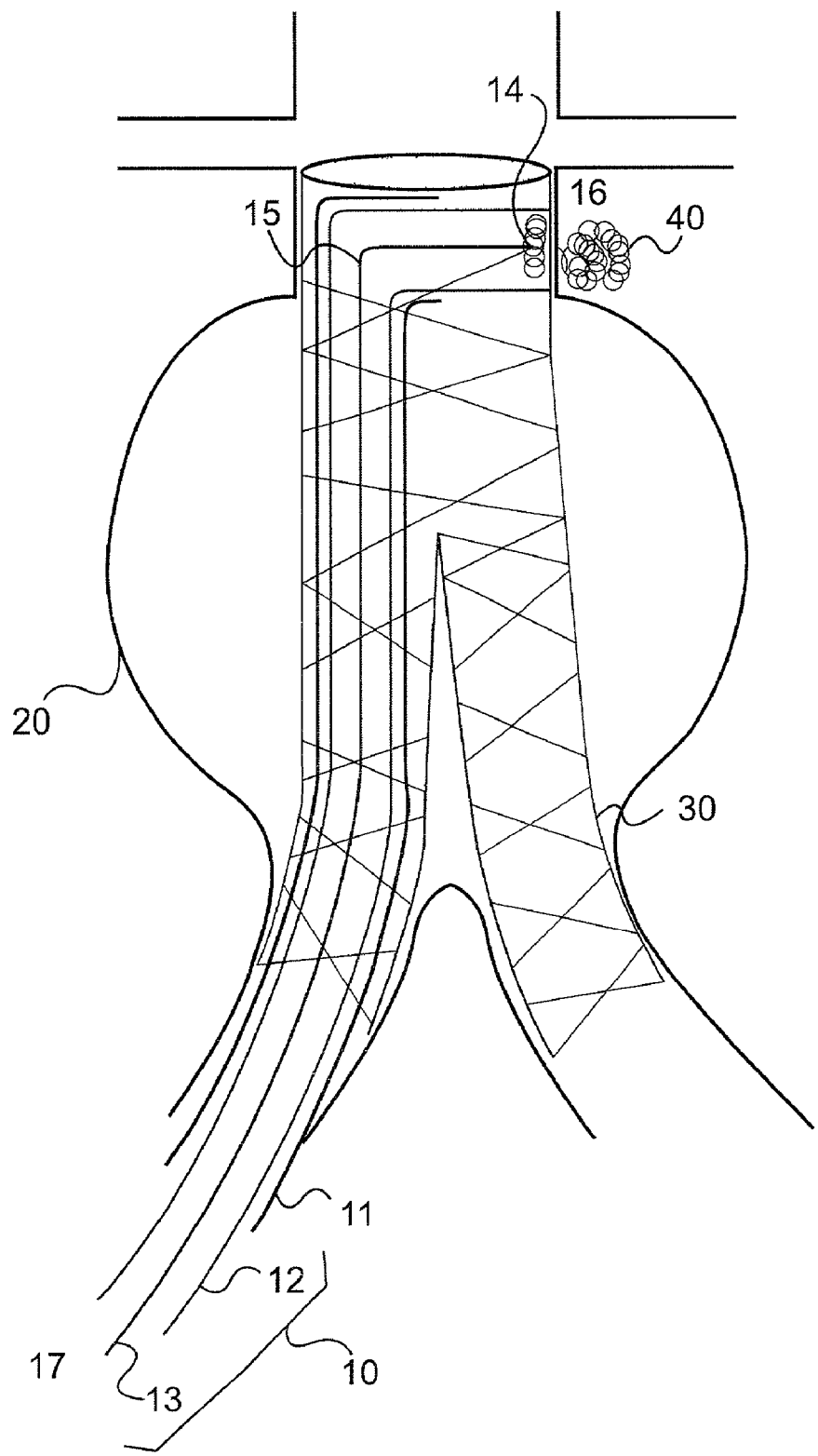
FIG. 1 is a longitudinal view of an embodiment of the present invention with a supported prosthetic.
Figure 2A:
FIG. 2 is a schematic of several embodiments of the present invention.
Figure 2B:
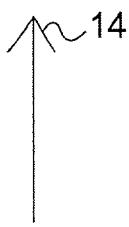
Figure 2C:
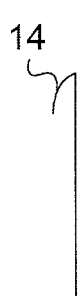
Figure 2D:
Figure 2E:
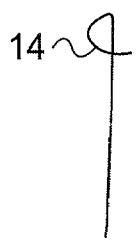
Figure 2F:
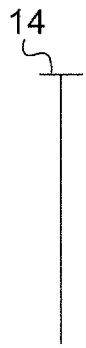
Figure 2G:
Figure 2H:
Figure 2I:
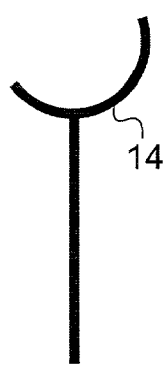
Figure 2J:
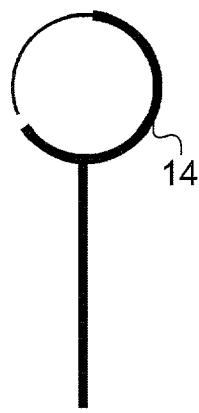

A fastener remover 10 in accordance with an embodiment of the present invention is disclosed in FIG. 1. A fastener 40 with a spring assembly of coils interposed between a supported prosthetic graft 30 and a vessel wall 20 is illustrated. FIG. 1 also depicts an embodiment of the fastener remover 10 comprising an outer catheter 11, an inner sheath 12, and a gripping member 13. The fastener remover 10 may be variable in length, diameter, shape, or may be any other suitable dimension, to complement the fastener 40 to be removed.

According to the embodiment shown in FIG. 1, the outer catheter 11 comprises a hollow passage having a distal end 16 and a proximal end 17. The outer catheter 11 may comprise any suitable material for surgical procedures. The inner sheath 12 housed within the outer catheter 11 may extend from the outer catheter's distal end 16 to the proximal end 17. The inner sheath 12 may comprise any suitable material for surgical procedures. The inner sheath may also be sized to accommodate a plurality of fasteners. The gripping member 13 comprises a connector portion 14 and an elongated stem 15. The connector portion 14 engages the fastener to be removed. As depicted in FIG. 2, the connector portion 14 may be in the shape of, but is not limited to: a hook, a plurality of longitudinally extending flanges, a spike, forceps, a retractable ring, or may be any other suitable connector portion able to engage the fastener to be removed. The connector portion 14 may function to extract or sever the spring assembly of coils. The connector portion 14 may comprise any suitable material for surgical procedures, such as, but not limited to, stainless steel, nitonol, any shape memory metal, or any other suitable material. The elongated stem 15 may comprise any suitable material for surgical procedures, such as, but not limited to, stainless steel, nitonol, any shape memory metal, or any other suitable material.

In an alternative embodiment of the present invention the fastener remover 10 may further comprise a cutting member to sever the fastener.

Specifically, the fastener remover 10 may be able to extract or sever a plurality of recently inserted fasteners 40 without damaging the supported prosthetic graft 30 to avoid having to discontinue a repair procedure and convert into an open operation.

It will be apparent to those skilled in the art that various modifications and variations can be made in the construction and configuration of the present invention, without departing from the scope or spirit of the invention. For example, the fastener remover may comprise a single catheter sheath or any number of catheter sheaths for delivery of the gripping member to the surgical site. Also, the inserted fastener to be removed may have a non-coiled configuration, such as, for example, a body portion and fastener legs. Thus, it is intended that the present invention cover the modifications and variations of the invention, provided they come within the scope of the appended claims and their equivalents.

What is claimed is:

1. A method of extracting an inserted fastener having a spring assembly of coils disposed between a surgical component and a vessel wall at a surgical site with a fastener remover, comprising the steps of:

orienting at least one flexible sheath of the fastener remover with the fastener to be removed;

gripping a portion of the spring assembly with a connector portion of the fastener remover; and adding a force with the fastener remover to disengage the fastener such that the fastener is removed from the surgical site.

2. The method according to claim 1, wherein the step of adding a force with the fastener remover to disengage the fastener further comprises the step of pulling the fastener through the surgical component and the vessel wall between which the fastener was interposed.

3. The method according to claim 1, wherein the step of engaging the fastener remover further comprises the step of severing the fastener with a cutting member of the fastener remover.

4. The method according to claim 3, wherein the step of severing the fastener further comprises the step of severing the fastener flush with the surgical component.

* * * * *